(12) United States Patent
Schedler et al.

(10) Patent No.: US 11,779,686 B2
(45) Date of Patent: Oct. 10, 2023

(54) COATING FOR MEDICAL DEVICES

(71) Applicant: Phenox GmbH, Bochum (DE)

(72) Inventors: Uwe Schedler, Neuenhagen (DE); Christian Heise, Brandenburg (DE); Thomas Thiele, Berlin (DE); Hans Henkes, Stuttgart (DE); Hermann Monstadt, Bochum (DE); Ralf Hannes, Dortmund (DE); Tim Lenz-Habijan, Herne (DE); Catrin Bannewitz, Bochum (DE)

(73) Assignee: Phenox GmbH, Bochum (DE)

( * ) Notice: Subject to any disclaimer, the term of this patent is extended or adjusted under 35 U.S.C. 154(b) by 539 days.

(21) Appl. No.: 16/612,994

(22) PCT Filed: May 17, 2018

(86) PCT No.: PCT/EP2018/062848
§ 371 (c)(1),
(2) Date: Nov. 12, 2019

(87) PCT Pub. No.: WO2018/210989
PCT Pub. Date: Nov. 22, 2018

(65) Prior Publication Data
US 2020/0215238 A1    Jul. 9, 2020

(30) Foreign Application Priority Data

May 17, 2017 (DE) .................. 10 2017 110 748.7
May 24, 2017 (DE) .................. 10 2017 111 486.6

(51) Int. Cl.
| A61L 33/04 | (2006.01) |
| A61L 31/02 | (2006.01) |
| A61L 31/10 | (2006.01) |
| A61L 31/16 | (2006.01) |
| A61L 33/00 | (2006.01) |

(52) U.S. Cl.
CPC ............ *A61L 33/04* (2013.01); *A61L 31/022* (2013.01); *A61L 31/10* (2013.01); *A61L 31/16* (2013.01); *A61L 33/0088* (2013.01); *A61L 2300/216* (2013.01); *A61L 2420/06* (2013.01)

(58) Field of Classification Search
None
See application file for complete search history.

(56) References Cited

U.S. PATENT DOCUMENTS

| 2007/0065483 | A1* | 3/2007 | Chudzik | ............... A61L 29/085 |
| | | | | 424/488 |
| 2008/0004410 | A1 | 1/2008 | Lai et al. | |
| 2009/0317443 | A1* | 12/2009 | Willis | ..................... A61L 31/14 |
| | | | | 424/423 |
| 2014/0249614 | A1* | 9/2014 | Levi | ......................... A61F 2/07 |
| | | | | 623/1.11 |

FOREIGN PATENT DOCUMENTS

WO    WO2008006911    1/2008

OTHER PUBLICATIONS

International Search Report from International Application No. PCT/EP2018/062848 dated Sep. 13, 2018.

* cited by examiner

*Primary Examiner* — Patricia Duffy
*Assistant Examiner* — Garen Gotfredson
(74) *Attorney, Agent, or Firm* — Crockett & Crockett, PC; K. David Crockett, Esq.

(57) ABSTRACT

A medical device substrate with a coating including a functional layer located on the substrate, with the functional layer including at least one sugar alcohol and being bonded to the substrate directly or indirectly via a functionalization of the sugar alcohol. Alternatively, the functional layer may also include other saccharides, in which case it is essential that polymerization of the saccharides takes place only upon bonding to the substrate. The inventive medical device exhibits reduced platelet adhesion and aggregation.

14 Claims, 1 Drawing Sheet

COATING FOR MEDICAL DEVICES

FIELD OF THE INVENTIONS

The invention relates to a coating for medical devices, said coating essentially comprising biomimetic and/or biorepulsive properties. Aside from this, the invention also relates to a method for the coating of medical devices.

BACKGROUND

The use or application of medical devices for the treatment of various disease patterns is constantly increasing. During relevant treatment, many of these medical devices enter the vascular system or more generally the patient's body at least temporarily or even remain there permanently, and thus come into direct contact with the patient's blood. As a result, the blood and its relevant constituents regularly cause reactions in the body which as a rule are undesirable, endanger the success of the treatment and may even lead to life-threatening consequences for the patient.

One of these undesirable adverse reactions to which a patient may be exposed concerns the blood coagulation caused by the medical devices used in the treatment and, specifically, the adhesion and aggregation of thrombocytes. The adhesion and the aggregation of thrombocytes (also called platelets) and thus the formation of blood clots, so-called thrombi, can be observed in permanent or temporary implants as well as in medical instruments that are only introduced into a patient's body for a short time for the purpose of treatment or diagnosis. The thrombocytes adhere to the surface of the introduced medical device/product marked by the body's endogenous proteins (thrombocyte adhesion), which as a result may lead to the formation of a thrombus (thrombocyte aggregation).

If such a thrombus, for example, is caused to be set free in the vascular system, it may give rise to very severe or even fatal secondary complications. This is primarily the case if the detached thrombus is washed away and in the form of an embolus comes to rest in smaller vessels, most effectively obstructing these and as a consequence causing the sufficient perfusion of the affected areas to be endangered. Resulting disease states may involve, for example, strokes, heart attacks or thromboses.

With a view to minimizing these risks for the patient, dual platelet inhibition is nowadays common practice as a rule to reduce the risk of thrombosis in the event surgery or interventions are necessary. For this purpose, the patient is usually given a first dose of a combination of platelet aggregation inhibitors, in particular a combination of acetylsalicylic acid (ASA) and clopidogrel, before the intervention or surgery and must continue to take these regularly for a certain period of time after the procedure. Aside from this, other platelet aggregation inhibitors mentioned in the relevant guidelines on dual platelet inhibition may also be put to use. These are usually applied instead of the clopidogrel in combination with ASS. Examples are prasugrel or ticagrelor.

The disadvantage of the dual platelet inhibition procedure is that it is systemic and therefore also has a systemic effect. For the duration of the dual platelet inhibition, the patient thus faces a higher bleeding risk as a whole.

What is more, there is another drawback in that dual platelet inhibition is not available for some patient groups because the risks associated with a dual platelet inhibition treatment, in particular the increased risk of bleeding, are so significant that these a priori outweigh the benefits that could be expected. In extreme cases, some patients may not even have access to certain treatment methods simply because they cannot be adequately protected against the risk of clot formation after an intervention has taken place. For example, a dual platelet inhibition treatment is established practice adopted after the implantation of endovascular prostheses (stents and the like).

It would therefore be desirable to be able to make available a medical device which the body does not recognize as a foreign object or which at least does not produce any undesirable reactions, such as blood coagulation reactions, which would be detrimental to the success of the treatment, and thus to be able to dispense with a dual platelet inhibition treatment when making use of such medical devices.

SUMMARY

It is thus the objective of the present invention to provide a medical device which does not essentially have the disadvantages described above.

Moreover, it is the objective of the invention to provide a coating for medical devices which imparts, in particular, biomimetic and/or biorepulsive properties to the surface of medical devices and to the extent possible does not trigger thrombocyte reactions, especially thrombocyte/platelet adhesion.

This objective is achieved by an invention comprising the characteristics of the independent claims 1 and 9. Advantageous embodiments in each case are the subject of the dependent claims. It is to be noted that any features and characteristics individually included in the claims may also be combined with each other in an optional and technologically sensible manner so that they reveal further implementations or methods of the invention.

DETAILED DESCRIPTION OF THE INVENTIONS

Figure 1:
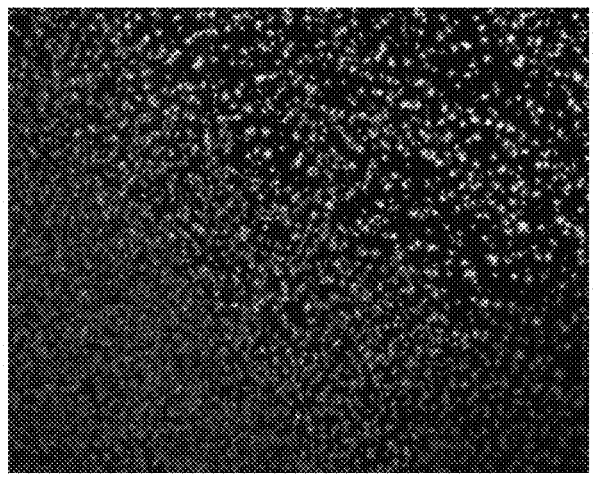
FIGS. 1 and 2 are photographs of plate specimens showing the difference in platelet adhesion between an uncoated plate and a coated plate.

A medical device as proposed by the invention essentially comprises at least a substrate and a functional layer. Preferably, the functional layer exhibits biomimetic and/or biorepulsive properties.

For many years, drug-coated implants have been known to take a different approach to avoiding the defense response of the body. In particular, anti-proliferative drug-coated stents should be mentioned here which, in contrast to the invention herein described, reduce neointimal hyperplasia.

In accordance with the present invention, the substrate itself is usually still covered by a carrier layer, which comprises adhesion promoters, by means of which the functional layer can be bonded to the substrate. Within the scope of the invention, preferred adhesion promoters are silane adhesion promoters. Alternatively, other adhesion promoters, for example polyolefinic adhesion promoters or adhesion promoters based on titanates or zirconates may also be employed.

Further examples of adhesion promoters include
  Thiols and dithio compounds, particularly suitable for precious metal substrates
  Amines and alcohols, especially suitable for platinum substrates Carboxylic acids, especially suitable for silver substrates and aluminum substrates; the aluminum substrate may have an aluminum oxide surface Phosphonic acids (phosphonates), especially suitable for iron, iron oxide, titanium and titanium dioxide substrates Complexing adhesion promoters, particularly chelates, which to some extent also bind non-covalently to substrates, particularly suited for various metal and metal oxide substrates In all cases, the adhesion promoters should comprise functional groups via which the adhesion promoter is capable of reacting with the functional layer, so that as a rule covalent bonding is possible.

Preferably, the substrate shall allow bonding to take place with an adhesion promoter. For the purposes of this application, such substrates shall be referred to as 'coatable substrates'. Accordingly, coatable substrates comprise substrates the surface of which is sufficiently reactive and/or sufficiently activatable to at least partially form bonds with an adhesion promoter or also directly with the functional layer. The bonds between the substrate and adhesion promoter preferably comprise covalent bonds.

Within the meaning of the present invention, coatable substrates may therefore be of very different nature and, in particular, comprise oxidizable substrates and combinations thereof. For example, these are metals such as nickel, titanium, platinum, iridium, gold, cobalt, chromium, aluminum, iron or alloys as well as combinations thereof. A metal may also be coated with another metal for instance, with the carrier layer and the functional layer being applied to the outer metal layer. Substrates in which the basic metal is covered by an oxide layer shall also count among coatable metals. Other coatable substrates are glasses.

Coatable substrates within the meaning of the present invention may also be various plastics, such as polyamides (PA), polytetrafluoroethylene (PTFE), expanded polytetrafluoroethylene (ePTFE), polylactides (PLA), polyester, polyether, polyurethane, polyolefins, as well as relevant block copolymers. In the field of medical technology, those skilled in the art are familiar with a large number of suitable plastics. Whereas, as a rule, an adhesion promoter is needed for metallic or oxidic surfaces, it is not always employed when polymers are used as substrate.

For example, an appropriate adhesion promotion may be achieved by silanization, that is the chemical bonding of silicon compounds, in particular silane compounds, to at least parts of their surface. On surfaces, silicon and silane compounds attach, for example, to hydroxy and carboxy groups.

Also useful as adhesion promoters are polyolefins which include chlorinated polyolefins (CPO) or acrylated polyolefins (APO).

The present invention, however, is not limited to coatings of the plastics and metals named hereinbefore, which in fact are to be understood only as examples. In principle, the invention is aimed at coatings of all conceivable materials that constitute a coatable substrate within the meaning of this invention.

Silane compounds within the meaning of the invention are all those compounds which follow the general formula $R_mSiX_n$ (m, n=0-4, where R stands for organic radicals, in particular alkyl, alkenyl or aryl groups, and X stands for hydrolyzable groups, in particular OR, OH or halogen, with R=alkyl, alkenyl or aryl). In particular, the silane may have the general formula $RSiX_3$. Moreover, for the purposes of the invention relevant compounds having several silicon atoms also count among the silane compounds. In particular, silane derivatives in the form of organosilicon compounds are regarded as silane compounds in accordance with the invention. Accordingly, silane compounds in the sense of the invention are not only to be understood as substances comprising a silicon skeleton and hydrogen and being designated as silanes.

Preferably, the matrix of the functional layer is covalently bonded to the carrier layer or substrate and is preferably synthesized by graft polymerization, with the functional layer being produced on the carrier layer or substrate. The polymerization of the applied monosaccharides, with reduction and oxidation products of monosaccharides also being understood as such, in particular sugar alcohols (alditols), essentially occurs preferably only on the carrier layer/the substrate or, resp., within the functional layer.

With respect to the purposes of the invention, it is irrelevant in which form the (graft) polymerization takes place. Therefore, growth of the side chains may in particular start from a main chain. This approach is also known as "grafting from". Another possibility is that the side chains have already started with the oligo- or polymerization and the already growing side chains are linking to the main chain ("grafting onto"). After all, already oligomerized or polymerized main and side chains may also link together ("grafting through").

Preferably, the functional layer substantially comprises a complex, highly branched, hydrophilic matrix consisting of a plurality of molecules each having a main chain as polymer backbone with each having a plurality of side chains. The main and/or side chains may form bonds with other main and/or side chains. Other matrix-forming mono-, oligo- and polymers can be integrated into these main and side chains without being themselves covalently bonded to the carrier layer.

The main chain may comprise at least partially polymerized vinyl, allyl, acrylic or methacrylic compounds or derivatives thereof and/or isomers thereof or combinations thereof.

The side chains particularly comprise mono- and/or oligosaccharides, with reduction products of mono- or oligosaccharides being also understood as such, in particular sugar alcohols (alditols). Aside from this and for the purposes of the present invention, oxidized mono- and/or oligosaccharides may also occur, with the oxidized form also being understood as mono- or oligosaccharide.

The medical device proposed by the invention comprises at least a substrate with a coating, said coating preferably comprising a carrier layer present on the substrate and a functional layer present on the carrier layer. The carrier layer essentially comprises the adhesion promoters, which in most cases are covalently bonded to the substrate. Moreover, non-covalently bonding adhesion promoters are also known, for example those that attach to the substrate via a complex bond. Preferred adhesion promoters are silicon compounds and polyolefinic adhesion promoters. As per a preferred embodiment, the functional layer comprises at least one functionalized sugar alcohol, via which the functional layer is covalently bonded to the carrier layer.

A preferred sugar alcohol of the functional layer corresponds in its non-functionalized form to a sugar alcohol of the molecular formula $C_6H_{14}O_6$, for example sorbitol, and/or its derivatives, for example sorbitan, and/or its isomers, such as for instance mannitol.

"In its non-functionalized form" means that the molecular formula referred to represents the molecular formula of the non-functionalized sugar alcohol, but should also include, where appropriate, its derivatives and/or isomers. The term functionalization shall be understood to indicate the introduction of a function into the compound permitting an attachment to the substrate, the carrier layer and/or to compounds already attached previously to the carrier layer or substrate.

Those skilled in the art are of course aware of the fact that the functional layer that forms part of the invention also comprises functionalized variants of the sugar alcohol of the molecular formula $C_6H_{14}O_6$ and/or its derivatives and/or its isomers. It is particularly clear to those skilled in the art that the functional layer comprises a complex matrix that can be created by polymerization of the applied, functionalized sugar alcohols.

Within the meaning of the invention and in addition to the definition generally used in chemistry of the term as "derived substance of similar structure", derivatives shall be understood to comprise, in particular, all cyclic and/or heterocyclic compounds derivable from the substance, and shall even more precisely comprise all cyclic and heterocyclic compounds that can be derived from the substance by dehydration. Furthermore, the oxidized form of a compound is also regarded as a derivative.

Preferably, the relevant sugar alcohol or the sugar alcohols are functionalized via at least one reactive group, wherein the reactive group preferably comprises a reactive multiple, in particular double bond and wherein said reactive double bond is preferably an acrylic group. Other functional groups that can be suitably used for polymerization and do not necessarily have to have a reactive double bond are known to those skilled in the art and, for instance, comprise methacrylic groups, vinyl groups or allyl groups.

Preferably, the sugar alcohols of the functional layer are at least partially polymerized among each other.

In a second preferred embodiment, the medical device comprises at least one substrate provided with a coating, with said coating comprising a functional layer. The functional layer comprises at least one functionalized monosaccharide, with the monosaccharides being covalently attachable to the carrier layer and oligomerizing or polymerizing taking place only upon bonding to the carrier layer.

Preferably, the coating comprises a carrier layer located on the substrate, with the functional layer in turn being bonded to the carrier layer. Particularly, the bonds formed may be covalent bonds, however, may also be other bonds such as complex bonds. The carrier layer comprises essentially the adhesion promoters that are bonded to the substrate. Preferred adhesion promoters are silicon compounds and polyolefinic adhesion promoters.

The monosaccharide of the functional layer preferably comprises at least one sugar alcohol and/or its derivatives and/or its isomers.

A preferred sugar alcohol of the functional layer corresponds in its non-functionalized form to a sugar alcohol of the molecular formula $C_6H_{14}O_6$, such as sorbitol, and/or its derivatives, for example sorbitan, and/or its isomers, for instance mannitol. The structure of sorbitol is shown below:

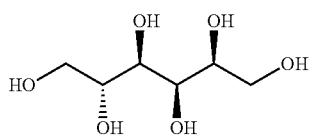 [SMILES: OC[C@@H](O)[C@@H](O)[C@H](O)[C@@H](O)CO]

It is to be noted that the phrase "in its non-functionalized form" shall mean that the molecular formula indicated represents the molecular formula of the non-functionalized sugar alcohol, but shall also comprise, where applicable, its derivatives and/or isomers It is clear to those skilled in the art that the functional layer that forms part of the invention comprises functionalized variants of the sugar alcohol of molecular formula $C_6H_{14}O_6$ and/or its derivatives and/or its isomers. Those skilled in the art are particularly aware of the fact that the functional layer comprises a complex matrix that has been created by polymerization of the applied, functionalized monosaccharides.

Preferably, the monosaccharides of the functional layer can at least be partially polymerized among each other.

Preferably, the monosaccharide is preferably functionalized via at least one reactive group, wherein the reactive group preferably comprises a reactive multiple bond, in particular a double bond, and wherein said reactive double bond preferably is an acrylic group. Other function groups that can be suitably employed for polymerization and do not necessarily have to have a reactive double bond are known to those skilled in the art and, for instance, comprise methacrylic groups, vinyl groups or allyl groups.

Therefore, the solution from which the functional layer of the coating proposed by the invention is made up may comprise one or a multitude of the following substances:

(1) Sorbitol acrylates (composed of one or several acrylate group(s)), the acrylate group(s) of which may be located at different positions.

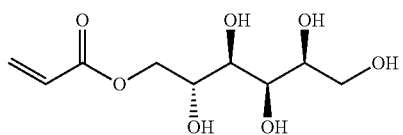

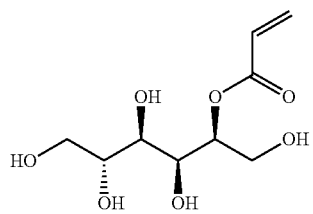

Sorbitol monoacrylates

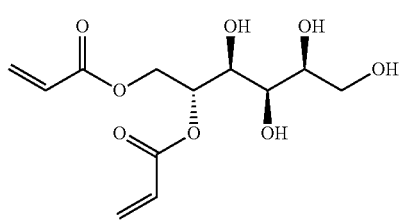

Sorbitol diacrylate

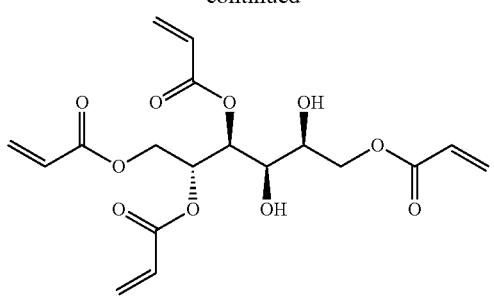

Sorbitol tetraacrylate (2) Sorbitol acrylates (comprising one or a multitude of acrylate group(s)), wherein the sorbitol acrylates may be partially oxidized and may comprise an aldehyde, keto and/or carboxy group.

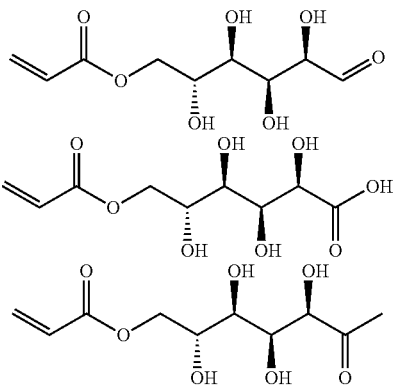

(3) Sorbitol acrylates (with one or a multitude of acrylate group(s)), which may comprise further reactive groups such as carboxy groups.

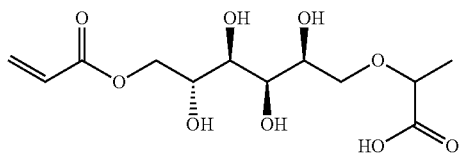 [SMILES: C=CC(=O)OC[C@@H](O)[C@@H](O)[C@H](O)[C@@H](O)COC(C)C(=O)O]

(4) Anhydrides, for example sorbitan (mono) acrylate comprising a polymerizable group.

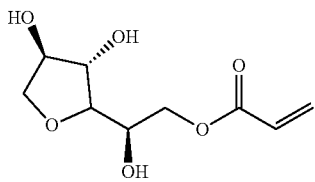

(5) Sorbitol having a non-polymerizable group, for example a carboxy group.

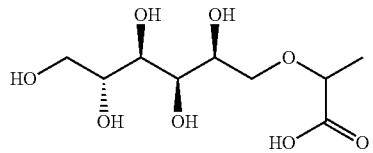 [SMILES: CC(OC[C@H](O)[C@@H](O)[C@H](O)[C@H](O)CO)C(=O)O]

(6) Complex sorbitol compounds that are not polymerizable but can be incorporated into the polymer matrix of the functional layer.

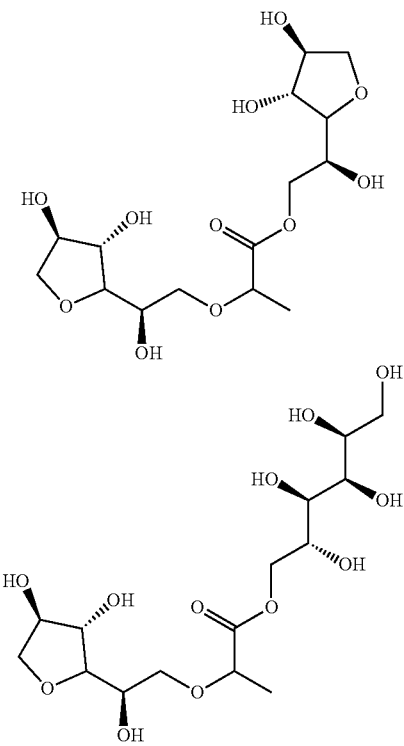

The structure of the functional layer can be varied via the specific composition of the substances. It is thus possible, for example, to create more closely meshed functional layers by increasing the proportion of crosslinkers or to create less crosslinked functional layers with longer linear ranges by causing the proportion of crosslinkers to be decreased.

Without the intention of wanting to follow a particular theory, the advantage of the inventive coating is seen in the fact that the functional layer possesses biomimetic or biorepulsive properties and is not recognized by thrombocytes as foreign to the body, but rather as originating within the body. Accordingly, the functional layer proposed by the invention does not trigger any reaction of the thrombocytes, in particular does not give rise to adhesion or aggregation reactions.

The biomimetic effect of the inventive coating is attributed to the fact that the functional layer claimed by the present invention imitates human glycocalyx. Glycocalyx coats the cells of blood vessels with a kind of mucus layer and consists of various polysaccharides that are covalently linked to the membrane proteins (glycoproteins) and membrane lipids (glycolipids).

Of advantage for the high biomimetic effect of the coating as proposed by the invention—and in particular of the functional layer—is that the polymerization of the reactants of the functional layer solution essentially occurs only after the functional layer solution has been applied to the substrate or carrier layer. As a result of the polymerization of the reactants a complex layer is thus created that is extremely similar to glycocalyx so that the adhesion of thrombocytes to surfaces provided with the inventive coating was found to be significantly lower than on uncoated surfaces.

The biorepulsive effect of the coating according to the invention is based on the principle of steric repulsion effects. Presumably, the space available to the oligomers and polymers on the surface is reduced when a protein intrudes on this space, i.e. an approaching protein forces the oligomers and polymers on the surface to adopt an energetically less favorable conformation. This results in an overall repulsive force acting on proteins. It is also possible that the displacement of water molecules from the coating results in a repulsive osmotic force acting against proteins.

As regards thrombocyte/platelet adhesion, this principle of action means that the adherence of thrombocytes is prevented because there are no or only a few proteins on the surface that are suitable for bonding so that the platelet adhesion is significantly reduced.

Another advantage of the inventive coating is that, via the intermediate step of adhesion promotion, the coating covers only those surfaces and structures of the medical device which are capable of being activated for the relevant adhesion promoters and in particular have in fact been activated. Upon application of the functional layer solution it is thus possible to place the complete medical device into the functional layer solution without having to additionally protect areas that are not to be coated.

Such a selective coating, respectively a coating process selectively carried out, offers advantages described hereinbefore for a plurality of medical devices and at least for those devices which are made of different materials, in which case the relevant coating is to be applied only on some of these materials.

The coating proposed by the present invention allows the coating process to activate only those parts/areas of the medical device that are intended to subsequently carry the functional layer. It is also conceivable that the medical device is already designed in such a way that the parts to be coated consist of substances that are capable of being activated for adhesion promotion.

Medical devices provided with the inventive coating are particularly suitable for endovascular, neurovascular and cardiovascular fields of application; however, the coating thus proposed by the invention can always be expediently applied on all medical devices that come into contact with blood.

ASSAYS

The inventive coating was subjected to a series of in vitro tests in order to ascertain the effectiveness of the coating proposed by the present invention. For this purpose, one uncoated small nitinol plate specimen and one small nitinol plate specimen silanized and subsequently coated with polymerized sorbitol acrylate in accordance with the invention were incubated with heparinized whole blood for a period of 10 minutes per test series. The adhesion of platelets was then determined by fluorescence microscopy with the aid of fluorescence-labelled CD61 antibodies.

The adhesion of platelets/thrombocytes to the nitinol plate specimens coated in accordance with the invention was found to be significantly lower than that of the uncoated nitinol plates.

FIG. 1 shows an uncoated small nitinol plate specimen after 10 minutes incubation time with heparinized whole blood at 10× magnification under the fluorescence microscope. The adhesion of a multitude of CD61 positive platelets is clearly visible.

Figure 2:
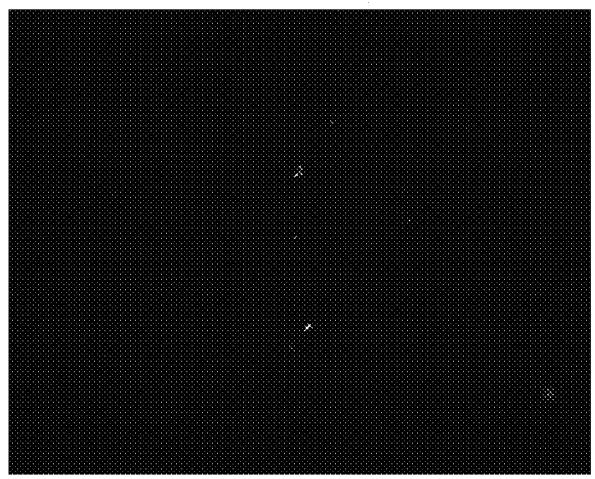

FIG. 2 shows a coated small nitinol plate specimen after 10 minutes incubation time with heparinized whole blood at 10× magnification under the fluorescence microscope. Only a few attached CD61 positive platelets can be recognized.

The invention claimed is:

1. A medical device comprising a substrate provided with a coating, wherein the coating comprises a functional layer and the functional layer comprises an oligomer or polymer made from a monosaccharide, characterized in that,
the monosaccharide from which the oligomer or polymer is made is linked directly or indirectly to the substrate via a functionalization of the monosaccharide and wherein the monosaccharide is oligomerized or polymerized only upon bonding of the monosaccharide to the substrate, wherein the monosaccharide in its non-functionalized form prior to oligomerization or polymerization comprises a sugar alcohol or a cyclic or heterocyclic compound that can be derived therefrom by dehydration.

2. The medical device according to claim 1, characterized in that the coating comprises a carrier layer which is located on the substrate and has an adhesion promoter, with the functional layer being bonded to the carrier layer.

3. The medical device according to claim 2, characterized in that the adhesion promoter is bonded to the substrate with a covalent bond and/or the functional layer is bonded to the carrier layer with a covalent bond.

4. The medical device according to claim 2, characterized in that the adhesion promoter comprises a silicon compound.

5. The medical device according to claim 1, characterized in that the sugar alcohol comprises a sugar alcohol of the molecular formula $C_6H_{14}O_6$.

6. The medical device according to claim 1, characterized in that the monosaccharide is functionalized with at least one reactive multiple bond that is responsible for the polymerization or oligomerization of the monosaccharide.

7. The medical device according to claim 6, characterized in that the reactive double bond is a constituent of a (meth) acrylic group.

8. The medical device according to claim 1, characterized in that the substrate comprises at least one metal selected from the group consisting of nickel, titanium, platinum, iridium, gold, cobalt, chromium, aluminum, iron and/or an alloy thereof.

9. The medical device according to claim 1, characterized in that the substrate comprises at least one plastic material selected from the group consisting of polyamides (PA), polytetrafluoroethylene (PTFE), expanded polytetrafluoroethylene (ePTFE), polylactides (PLA), polyester, polyether, polyurethane, polyolefins or block copolymers of polyamides (PA), polytetrafluoroethylene (PTFE), expanded polytetrafluoroethylene (ePTFE), polylactides (PLA), polyester, polyether, polyurethane, and polyolefins.

10. The medical device according to claim 1, characterized in that it is a medical device for endovascular applications.

11. The medical device according to claim 1, characterized in that it is a medical device for neurovascular applications.

12. The medical device according to claim 1, characterized in that it is a medical device for cardiovascular applications.

13. The medical device according to claim 7, characterized in that the at least one reactive multiple bond is a reactive double bond.

14. The medical device according to claim 4, characterized in that the silicon compound is a silane compound.

* * * * *